(12) United States Patent  (10) Patent No.: US 6,368,289 B2
Stone  (45) Date of Patent: Apr. 9, 2002

(54) ACOUSTIC COUPLING DEVICE

(75) Inventor: Robert T. Stone, Sunnyvale, CA (US)

(73) Assignee: Kinderlife Instruments, Inc., Mountain View, CA (US)

( * ) Notice: Subject to any disclaimer, the term of this patent is extended or adjusted under 35 U.S.C. 154(b) by 0 days.

(21) Appl. No.: 09/817,666

(22) Filed: Mar. 26, 2001

Related U.S. Application Data

(63) Continuation-in-part of application No. 09/782,550, filed on Feb. 13, 2001.
(60) Provisional application No. 60/182,279, filed on Feb. 14, 2000.

(51) Int. Cl.$^7$ .................................................. A61B 5/00
(52) U.S. Cl. ........................ 600/559; 181/129; 73/585
(58) Field of Search ........................... 600/559; 73/585, 73/587; 128/897; 181/129, 130, 135; 381/56, 58, 104, 124, 328

(56) References Cited

U.S. PATENT DOCUMENTS

| | | | | |
|---|---|---|---|---|
| 4,029,083 A | * | 6/1977 | Baylor | 600/559 |
| 4,677,679 A | * | 6/1987 | Killion | 381/74 |
| 5,105,822 A | * | 4/1992 | Stevens et al. | 600/559 |
| 5,916,174 A | * | 6/1999 | Dolphin | 600/559 |
| 5,923,764 A | * | 7/1999 | Shennib | 381/60 |
| 5,954,667 A | * | 9/1999 | Finkenzeller et al. | 600/544 |
| 6,129,174 A | * | 10/2000 | Brown et al. | 181/135 |
| 6,231,521 B1 | * | 5/2001 | Zoth et al. | 600/559 |

* cited by examiner

Primary Examiner—Kevin Shaver
Assistant Examiner—Charles Marmor, II
(74) Attorney, Agent, or Firm—Francis Law Group

(57) ABSTRACT

An acoustic coupling device for a hearing screening device comprising a coupling input adapted to removeably engage a hearing screening device, the coupling input being adapted to receive an acoustic stimulus from the hearing screening device and transmit at least one response signal from a subject (or patient) to the hearing screening device; a first passive attenuator adapted to attenuate a first frequency of the acoustic stimulus; a second passive attenuator adapted to attenuate a second frequency of the acoustic stimulus, the first and second passive attenuators in combination providing a second acoustic stimulus having a substantially balanced acoustic spectrum; at least a first earpiece disposed proximate the ear canal of one of the subject's ears, the earpiece including a stimulus input adapted to transmit at least the second acoustic stimulus to the subject and receive at least a first response signal having a first volume from the subject's ear; and a response signal compensator adapted to regulate the first volume of the first response signal.

14 Claims, 9 Drawing Sheets

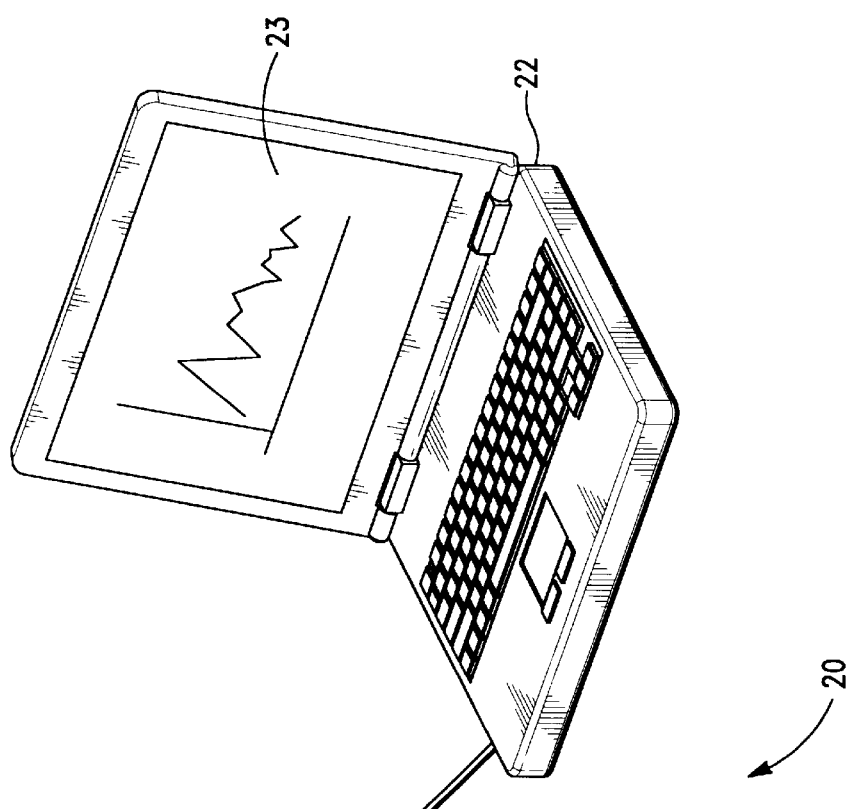
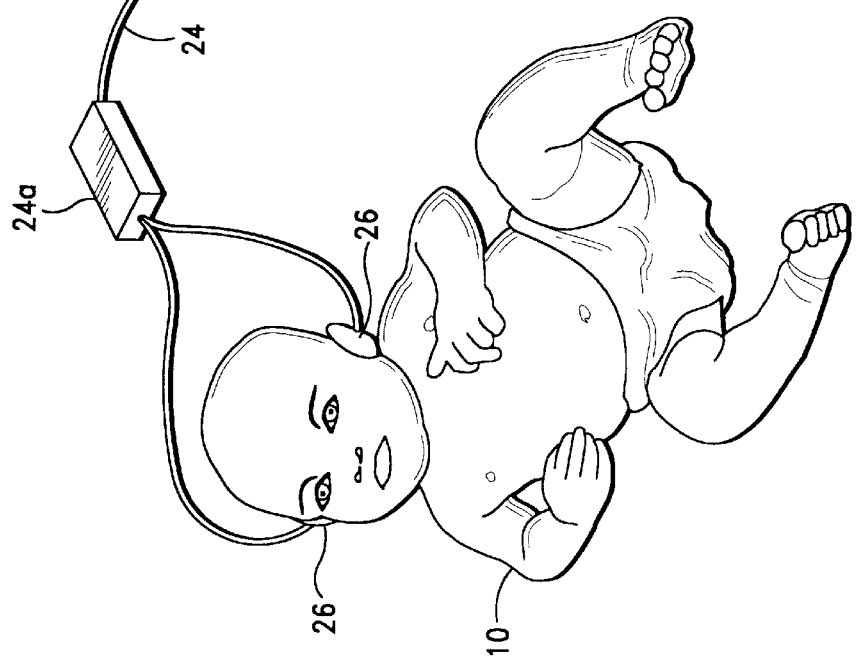
FIG.-1
(PRIOR ART)

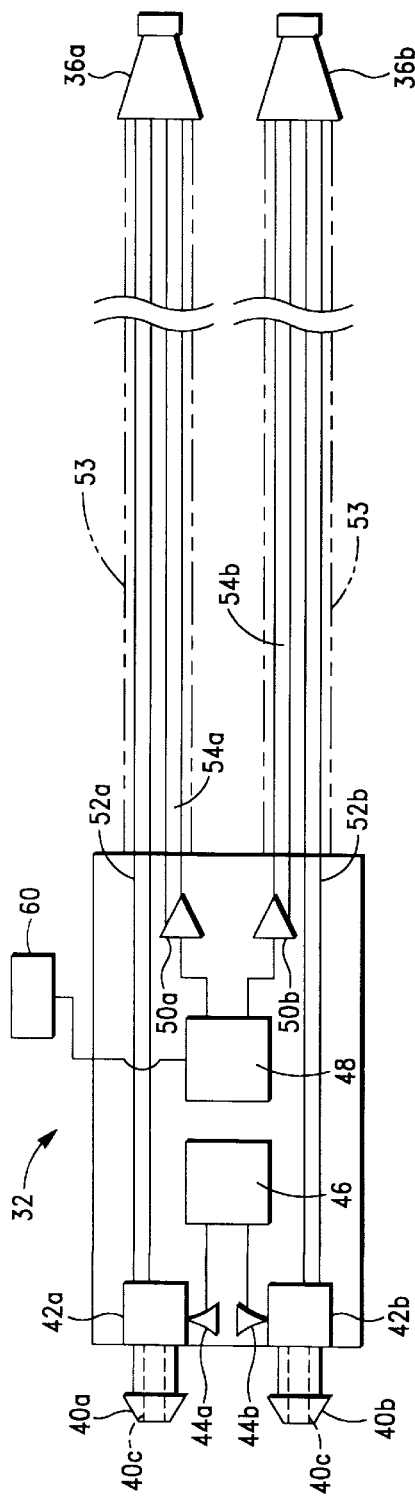
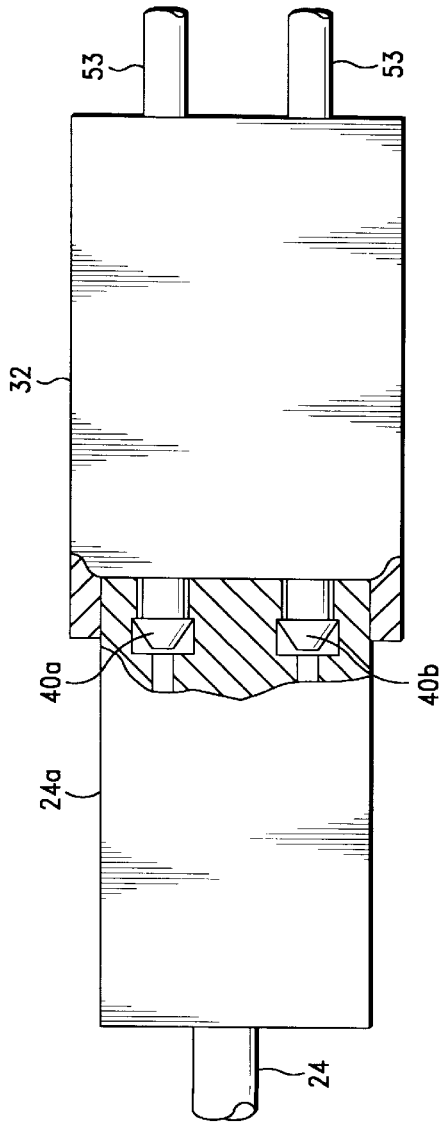

ACOUSTIC COUPLING DEVICE

CROSS REFERENCE TO RELATED APPLICATIONS

This Application is a continuation-in-part of U.S. application Ser. No. 09/782,550, filed Feb. 13, 2001, which claims the benefit of U.S. Provisional Application No. 60/182,279, filed Feb. 14, 2000.

FIELD OF THE INVENTION

The present invention relates generally to the field of audiometric devices and associated screening methods. More particularly, the invention relates to an acoustic coupling device for use in connection with equipment for stimulating the reaction to sound in a subject.

BACKGROUND OF THE INVENTION

Language acquisition in infants requires a critical period of hearing capacity, which spans the frequency range of human speech. The critical period extends from birth to about two to three years of age, when infants typically begin to talk with some level of proficiency.

Various hearing screening techniques have been developed over the years which present a sound input into the ear of a subject (i.e., infant) and detect a response to that input. The response is related to the characteristics of the sound input and the conditions inside the ear, the neural connections, and the vibration transmission mechanism of the ear.

In many instances, hearing screening is performed by using an earphone having a cavity that fits closely about the ear. Auditory tones or "clicks" are fed into the earphone cavity, and the response generated by the patient's ear and the neural conduction system in response to the auditory tones is sensed by a transducer. The transducer may be, for example, a microphone, suitable electrodes, piezo electric materials and like devices that generate signals representative of the response to the auditory input.

There are, however, several problems associated with the noted technique. A major problem is that ambient noises, internal or external to the cavity, are capable of interfering with the stimulus or the response signals and, hence, the results. In most cases, the monitoring equipment has mechanisms, such as microphones, for detecting and compensating for ambient background noise. Illustrative is the disposable earphone disclosed in U.S. Pat. No. 4,930,520 (Liverani), which is sold under the trademark Ear Couplers® by Natus Medical, Inc.

The Liverani earphone includes a toroidal baffle of anechoic, insulative foam, a clear planar window plastic sheet adhered to one side of the baffle defining a cavity, and an adhesive coating on the other side of the baffle for bonding the disposable earphone to the region surrounding the infant's ear. The earphone is employed with transducers for transferring acoustical energy through a pneumatic tube to the infant's ear for testing.

One of the problems with the Liverani device is that the earphone is somewhat cost-ineffective in that the entire earphone is not re-usable and must be disposed of after each use. Another problem with the device is that its construction is not capable of adjustment for infants with different size ears. As a result, it is necessary to manufacture different size earphones and maintain an inventory of the different sizes to obtain acceptable test performance for infants having different sized ears.

A further problem is that the Liverani device does not include any means for regulating or monitoring the amplitude of the stimulus presented to the infant.

In U.S. Pat. No. 5,913,309 a disposable earphone element is disclosed for use in hearing screening tests, which addresses some of the disadvantages associated with the Liverani device. The disposable element similarly includes an adhesive on one side of the element, which is adapted to adhere to the patient's skin around the ear. An adhesive is further provided on the opposite side of the element to temporarily adhere to the earphone. Thus, after a test is conducted, the disposable element is merely removed and replaced, allowing one to reuse the earphone.

Although the disposable element disclosed in the '309 eliminates the need to replace the entire earphone after each use, replacement of the disposable element is still somewhat cost-ineffective. Further, the disposable element does not include any means for regulating or monitoring the amplitude of the stimulus.

Finally, a problem associated with each of the noted devices is that the adhesive employed to adhere the devices to the skin is generally ineffective to maintain full contact with the infant during the period of hearing screening. Thus, ambient noise can, and in many instances will, enter into the cavity.

It is therefore an object of the present invention to provide an improved acoustic coupling device that overcomes the problems of prior art devices and, further, provides means for regulating and/or monitoring the amplitude of the stimulus presented to the subject.

SUMMARY OF THE INVENTION

In accordance with the above objects and those that will be mentioned and will become apparent below, the acoustic coupling device (or apparatus) in accordance with this invention comprises a coupling input adapted to engage a hearing screening device, the coupling input being adapted to receive an acoustic stimulus from the hearing screening device and transmit at least one response signal from a subject (or patient) to the hearing screening device; a first passive attenuator adapted to attenuate a first frequency of the acoustic stimulus; a second passive attenuator adapted to attenuate a second frequency of the acoustic stimulus, the first and second passive attenuators in combination providing a second acoustic stimulus having a substantially balanced acoustic spectrum; at least a first earpiece disposed proximate the ear canal of one of said subject's ears, the earpiece including a stimulus input adapted to transmit at least the second acoustic stimulus to the subject and receive at least a first response signal from the subject's ear, the first response signal having a first volume; and a response signal compensator adapted to regulate the first volume of the first response signal.

The method of testing the hearing of a subject in accordance with the invention comprises the steps of (a) presenting a first acoustic stimulus to a first passive attenuator, the first acoustic stimulus having at least first and second frequencies; (b) passively attenuating the first and second frequencies to yield at least a second acoustic stimulus having a substantially balanced acoustic spectrum; (c) transmitting the second acoustic stimulus to the inner ear of the subject; (d) detecting a first response signal from the subject's inner ear, the first response signal having a first volume; (e) regulating the first volume to a pre-selected second volume; and (f) detecting the first response signal having the second volume.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 1 is an illustration of a prior art hearing screening test device;

FIG. 3A is a schematic illustration of one embodiment of the acoustic coupling apparatus according to the invention;

FIG. 3B is a schematic illustration of the acoustic coupling apparatus showing the engagement of the acoustic coupling apparatus to the hearing screening device according to the invention;

DETAILED DESCRIPTION OF PREFERRED EMBODIMENTS

Figure 2:
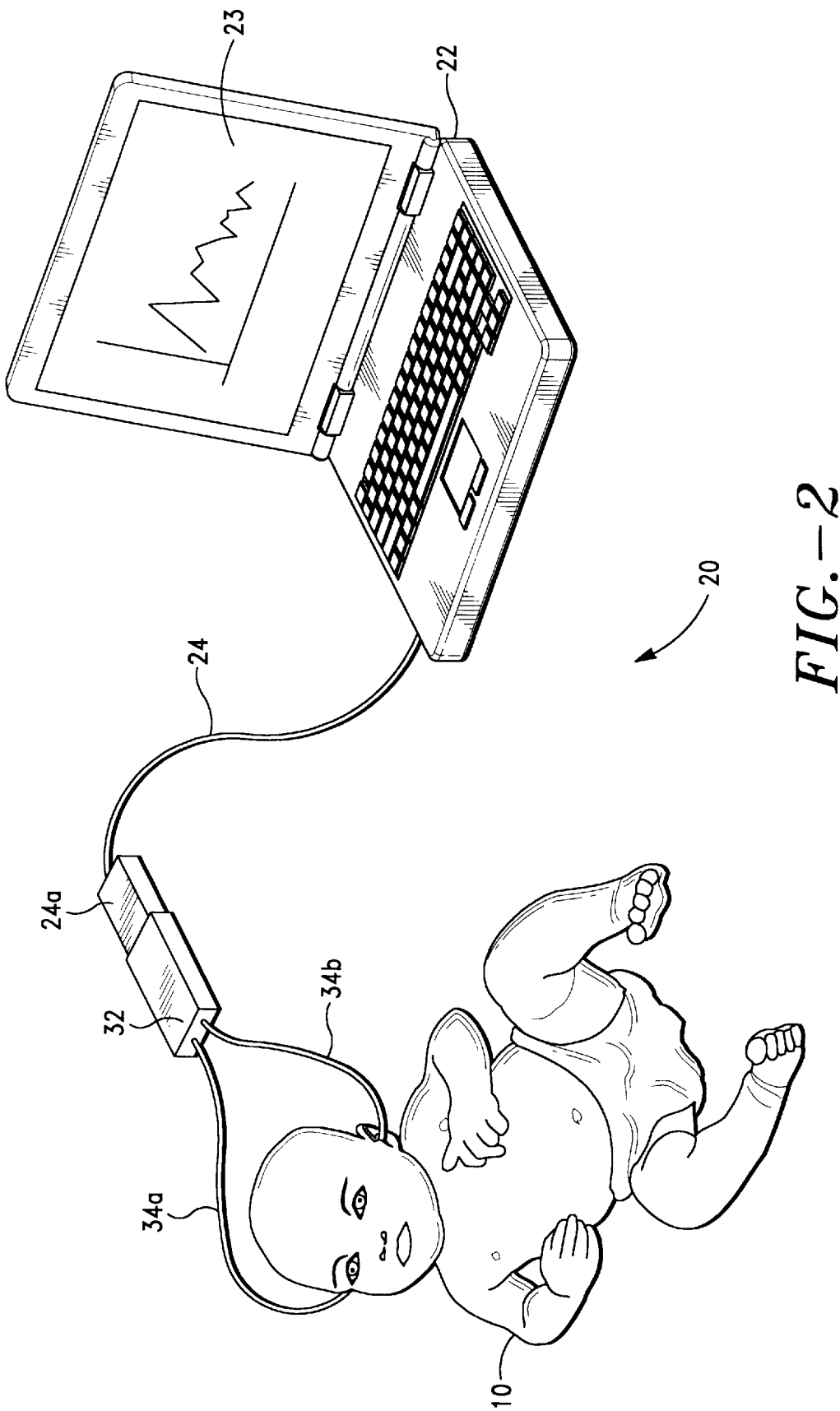
FIG. 2 is an illustration of the hearing screening device shown in FIG. 1, incorporating the acoustic coupling apparatus according to the invention.

The present invention substantially reduces or eliminates the disadvantages and drawbacks of prior art audiometric screening devices and systems. As discussed in detail below, in one embodiment of the invention the acoustic coupling device includes at least one disposable ear piece adapted to sealably engage a subject's ear canal (or cavity), passive attenuation means to present a stimulus having a substantially balanced acoustic spectrum to the subject, and engagement means adapted to facilitate the use of the invention on conventional hearing screening test devices.

Referring first to FIG. 1, there is shown a prior art audiometric screening device (or system) 20. The device 20 includes a laptop computer 22 having a monitor 23 for displaying one or more characteristics of the processed signals emanating from the subject 10. The device 20 also includes means for providing at least one acoustic stimulus signal and means for receiving response signals from the subject 10.

The audiometric screening system 20 further includes a probe 24 having a pair of earphone assemblies 26, such as that disclosed in U.S. Pat. No. 5,826,582, for presenting the acoustic stimulus signal(s) to the subject 10. The earphone assemblies 26 are also adapted to receive the evoked otoacoustic emission (OAE) response signal from the subject's ear.

As discussed above, two major drawbacks of the noted device are (i) the earphone assemblies 26 must be replaced after each test and (ii) the earphone assemblies 26 do not include any means for monitoring or regulating the stimulus and, in particular, the amplitude of the stimulus presented to the subject 10.

Referring now to FIG. 2, there is shown one embodiment of the acoustic coupling device 32 of the invention incorporated into the device shown in FIG. 1. As illustrated in FIG. 2, the audiometric coupling device 32 is adapted to engage and, hence, communicate with the conventional audiometric device 20 via probe 24 (see also FIG. 3B).

Referring now to FIG. 3A, there is shown a block diagram of a first embodiment of the acoustic coupling device 32. The coupling device 32 includes first and second inputs 40a, 40b having a lumen 40c therein adapted to receive and transmit the stimulus signal provided by the hearing screening device 20 to the Subject 10 via leads 34a and 34b. As illustrated in FIG. 3B, the first and second inputs 40a, 40b are further adapted to slideably and substantially sealably engage the probe connector 24a.

As illustrated in FIG. 3A, the acoustic coupling device 32 further includes a pair of acoustic attenuators 42a, 42b in communication with inputs 40a, 40b. The attenuators 42a, 42b are preferably adapted to provide at least first and second reductions in stimulus (i.e., signal) amplitude, respectively. In a preferred embodiment of the invention, the first and second reductions in stimulus amplitude are substantially equal.

According to the invention, various attenuators 42a, 42b may be employed within the scope of the invention to provide the first and second reductions in stimulus amplitude. Such attenuators include conventional orifices, tubing lengths and other acoustic impedance devices, which are incorporated by reference herein.

Referring back to FIG. 3A, disposed on the opposing end of each attenuator 42a, 42b and in communication therewith are primary stimulus input leads or tubes 52a, 52b. Also disposed proximate each attenuator 42a, 42b are first and second microphones 44a, 44b. The microphones 44a, 44b are in communication with the coupling device control means 46, which is adapted to control the operation (e.g., activation) of the acoustic coupling device.

According to the invention, the microphones 44a, 44b are positioned and adapted to monitor the primary stimulus input (i.e., acoustic stimulus signal) presented to the attenuators 42a, 42b. Each of the microphones 44a, 44b are also preferably adapted to provide at least a first signal to the control means 46 indicative of the presence of the stimulus. In response to the first signal(s), the control means 46, in the instant embodiment, would activate the coupling device 32 (i.e., on/off switch).

Figure 5:
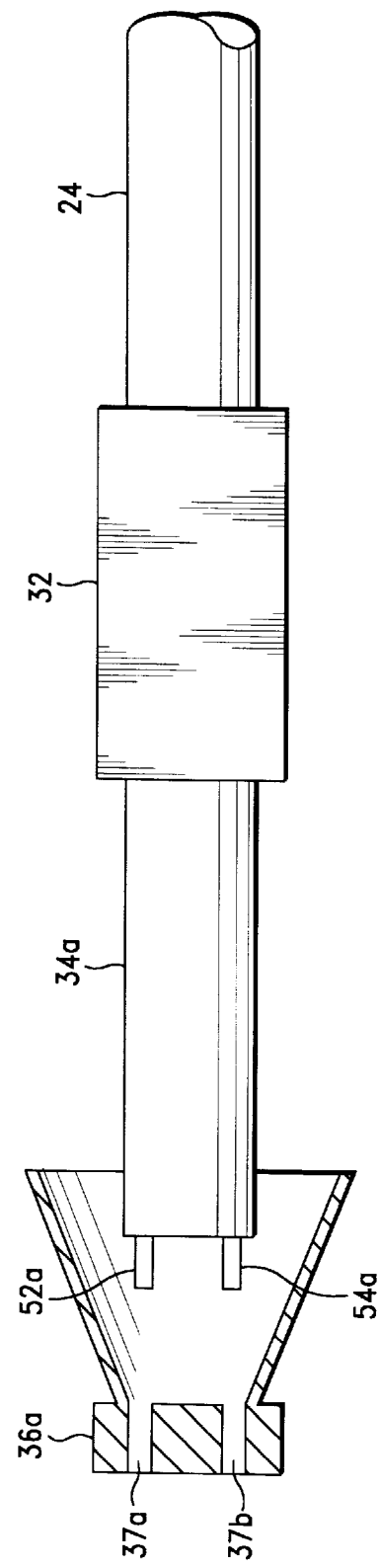
FIG. 5 is a sectional view of an earpiece according to the invention.

As illustrated in FIG. 3A, a first pair of input and output leads 52a, 54a, which are preferably encased in a cable housing 53 (shown in phantom), are in communication with a first earpiece 36a and a second pair of input and output leads 52b, 54b, which are similarly encased in a cable housing 53, are in communication with a second earpiece 36b. As illustrated in FIG. 5, each earpiece 36a, 36b is provided with an input and output lumen 37a, 37b adapted to slideably receive a respective one of the input 52a, 52b and output 54a, 54b leads.

In operation, a stimulus is presented to each of the subject's ears via input leads 52a, 52b and earpieces 36a, 36b. The stimuli are sensed and substantially simultaneously transmitted into and through leads 52a, 52b and communicated to microphones 50a, 50b via output leads 54a, 54b. The microphones 50a, 50b provide at least second and third signals in response to the detected (or response) stimuli, which are communicated to the monitoring means 48 of the invention.

According to the invention, the monitoring means 48 includes means for storing at least one stimulus amplitude indicative of an unacceptable response signal and means for comparing the unacceptable response signal to the response signal (i.e., detected stimulus or stimuli) from the subject 10. Various monitoring means, such as a conventional processor and comparator, may be employed within the scope of the invention. In a preferred embodiment, the monitoring means 48 comprises an A/D converter.

According to the invention, the monitoring means 48, in response to the second and third signals, is adapted to provide a plurality of signals, including at least a fourth signal indicative of an acceptable stimulus amplitude and a fifth signal indicative of an unacceptable stimulus amplitude.

In a preferred embodiment of the invention, at least one of the monitoring means signals are communicated to the coupling device display means 60. According to the invention, the display means 60 is adapted to provide a visual indication of the stimulus quality in response to the monitoring means signals.

As will be appreciated by one having skills in the art, various display means may be employed within the scope of the invention. In a preferred embodiment, the display means 60 comprises a conventional light emitting diode (LED) assembly.

Thus, by way of example, in response to the fourth signal referenced above, the display means 60 would illuminate a "green" light. In response to the fifth signal, the display means 60 would illuminate a "red" light.

Figure 4:
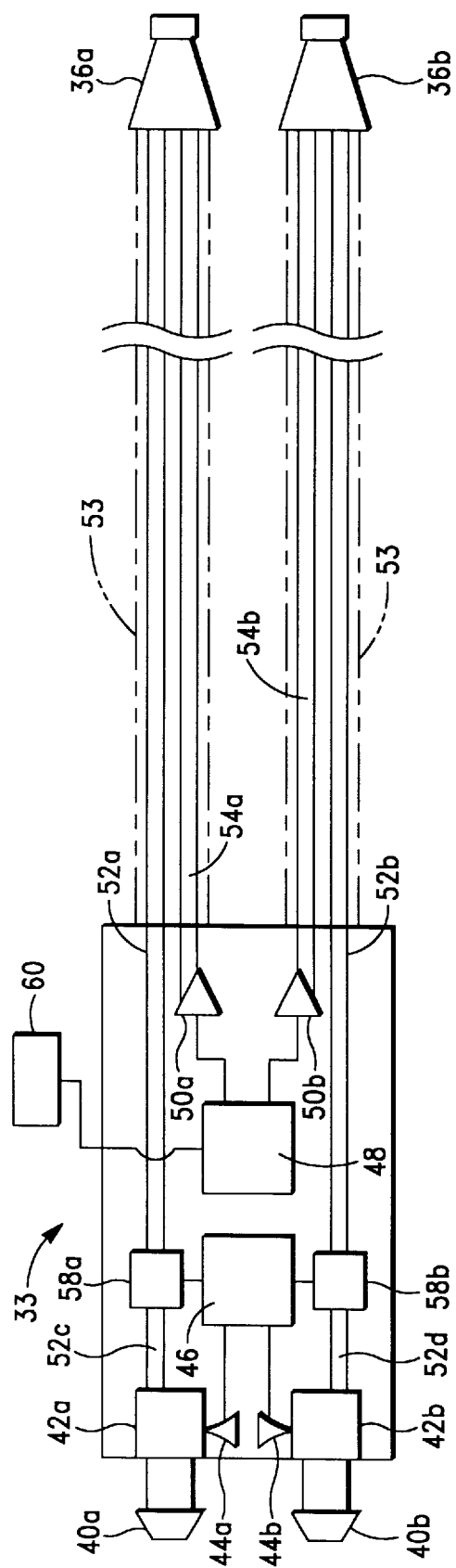
FIG. 4 is a schematic illustration of a further embodiment of the acoustic coupling apparatus according to the invention.

Referring now to FIG. 4, there is shown an additional embodiment of the acoustic coupling device, designated generally 33. In this embodiment, the device 33 further includes a pair of signal generators (or reproducers) 58a, 58b adapted to provide the desired amplitude of the stimulus.

As illustrated in FIG. 4, the signal generators 58a, 58b are in communication with the control means 46. According to the invention, the monitoring means 48 is also in communication with the control means 46. Thus, in operation, the monitoring means 48 would preferably provide at least sixth and seventh signals to the control means 46 indicative of the quality (or amplitude) of the stimulus signals detected by the microphones 50a, 50b, respectively. The control means 46, in response to the sixth and seventh signals, provides at least an eighth signal to signal generator 58a and at least a ninth signal to signal generator 58b. In response to the control means eighth and ninth signals, the signal generators 58a, 58b would increase or decrease the stimulus amplitude to an acceptable level.

As illustrated in FIG. 4, the signal generators 58a, 58b are in communication with input leads 52a, 52b. The signal generators 58a, 58b also include output leads 52c, 52d that are in communication with the first and second inputs 40a, 40b.

According to the invention, each of the noted audiometric coupling devices 32, 33 includes a pair of earpieces 36a, 36b that are adapted to be placed proximate or, more preferably, within the cavity of the subject's ear (i.e., one earpiece per ear) and engage the input and output leads 52a, 52b, 54a, 54b of the coupling device 32 (see FIG. 5). The earpieces 36a, 36b are preferably constructed out of a flexible polymeric material, such as low-density polyurethane.

As discussed, the earpieces 36a, 36b are provided with input and output lumens 37a, 37b that are adapted to slideably receive a respective one of the input 52a, 52b and output 54a, 54b leads. Thus, after use, the earpieces 36a, 36b can be readily removed and replaced.

Figure 6B:
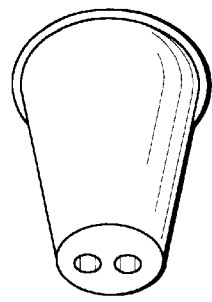
FIG. 6B is a perspective view of an additional embodiment of the earpiece according to the invention.
Figure 6A:
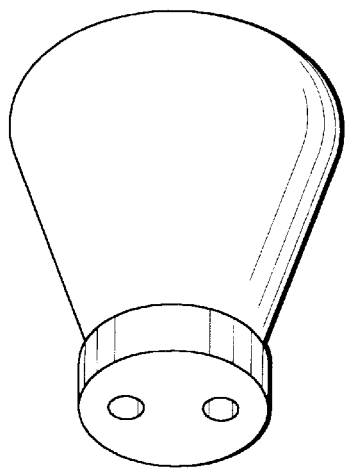
FIG. 6A is a perspective view of the earpiece shown in FIG. 5.

As will be appreciated by one having skill in the art, various configurations of the "low-cost" earpieces 36, such as the earpieces shown in FIGS. 6A and 6B, can be employed within the scope of the invention to provide an acceptable level of sealable engagement proximate the subject's ear canal.

Figure 7:
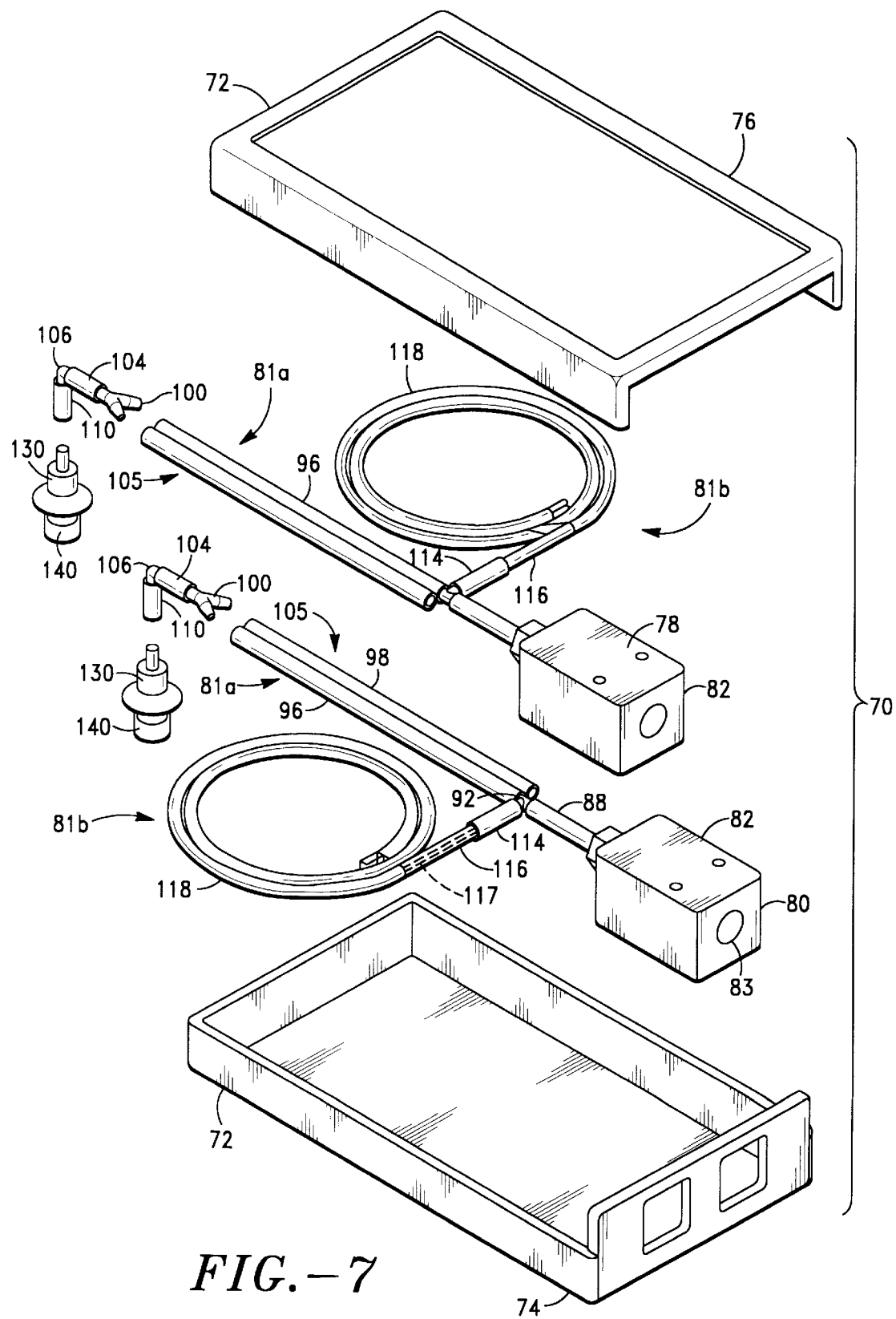
FIG. 7 is an exploded, perspective view of another embodiment of the invention.

Referring now to FIG. 7, there is shown a further embodiment of the acoustic coupling device 70. As discussed in detailed herein, in contrast to the electronic attenuation means employed in the embodiments described above, the present embodiment employs passive attenuation means to achieve a predetermined response characteristic. By the term "predetermined response characteristic", it is meant to mean a sound or signal transfer function expressed in terms of sound intensity (db) and frequency.

As illustrated in FIG. 7, the acoustic coupling device 70 includes a housing 72, having a bottom 74 and a top 76, and first and second attenuation systems 78, 80 disposed therein. The housing 72 is similarly adapted to slideably engage the probe connector 24a.

For simplicity, only the second attenuation system 80 will be described. However, it is to be understood that the first attenuation system of the noted embodiment 78 is similarly constructed and the description of the second attenuation system 80 is equally applicable to each system 78, 80.

Figure 8:
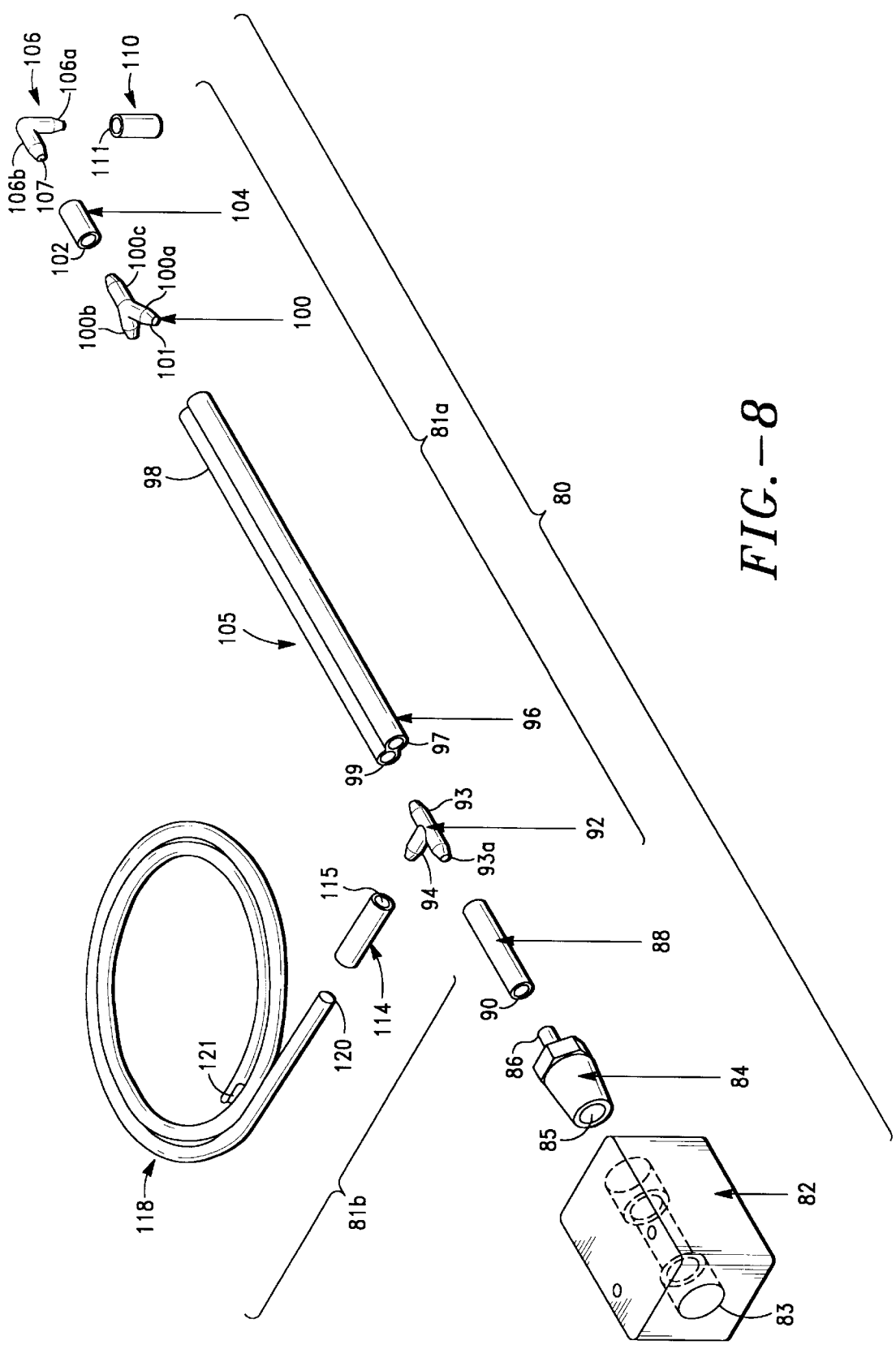
FIG. 8 is an exploded, perspective view of the passive attenuation system according to the invention.

Referring now to FIG. 8, there is shown an exploded view of the second attenuation system 80. The system 80 includes an input 82 having a lumen 83 therein similarly adapted to receive and transmit the stimulus signal provided by the hearing screening device 20.

As illustrated in FIG. 8, the system 80 further includes a coupler 84 that is adapted to engage the input 82, first and second attenuation means 81a, 81b and sound compensating means 105. The coupler 84 includes a substantially continuous lumen 85 therethrough that is in communication with the input lumen 83 and an outlet 86.

Figure 13:
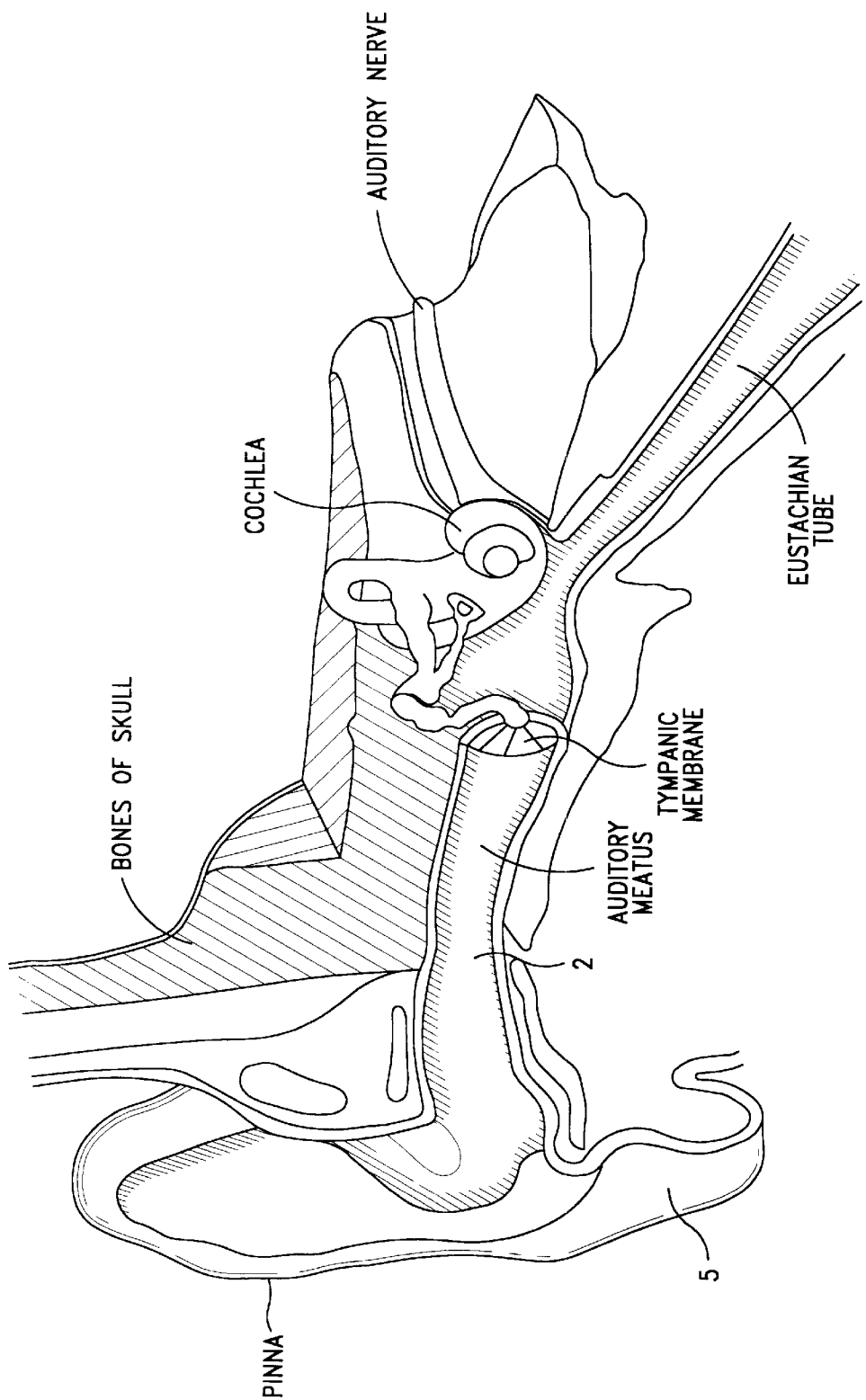
FIG. 13 is an illustration of a human ear.

As indicated above, a key feature of the noted embodiment is the unique passive attenuation means. According the invention, the attenuation means comprises first attenuation means 81 a adapted to substantially attenuate high frequency sound in the range of 2 KHz to 10 KHz approximately 90%, more preferably, in the range of 50 to 90% and second attenuation means 81b adapted to substantially attenuate low frequency sound in the range of 500 to 3 KHz approximately 90%, more preferably, in the range of 50 to 90%. As discussed in detail herein, the first 81a and second 81b attenuation means, in combination, yield a substantially balanced acoustic spectrum of sound that is transmitted to the inner ear 2 (see FIG. 13) of the subject.

Figure 10:
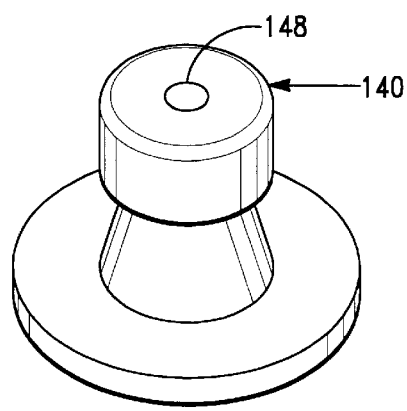
FIG. 10 is a perspective view of a further embodiment of an earpiece according to the invention.

Referring back to FIG. 8, the first attenuation means preferably includes (i) a first tube 88 having a lumen 90 therein, (ii) a second tube 96 having a lumen 97 therein, (iii) a third tube 104 having a lumen 102 therein, (iv) a fourth tube 110 having a lumen 111 therein, and (v) an earpiece 140 having an outlet 148 (see FIG. 10).

According to the invention, each lumen 90, 97, 102, 111, and the earpiece outlet 148, is adapted to transmit the stimulus signal transmitted by the hearing screening device 20 and the response signal(s) from the subject. Each lumen 90, 97, 102, 111 and the earpiece outlet 148 is also in communication with the coupling outlet 86 and, hence, coupling lumen 85. The noted communication is preferably achieved as follows.

Referring to FIG. 7, the first end of tube 88 is adapted to slideably engage coupling outlet 86. The second end of tube 88 and first end of tube 96 are adapted to slideably engage T-coupling 92.

As illustrated in FIG. 8, the T-coupling 92 includes a first substantially linear section 93 having a lumen 93a therein in communication with lumens 90, 97 when tubes 88, 96 are operatively engaged thereto. The T-coupling 92 further includes a second section 94 that is preferably disposed substantially perpendicular to the T-coupling section 93. The second section 94, which is adapted to engage and, hence, facilitate communication with the second attenuation means 81b of the invention, similarly includes lumen 93a which also extends into and through section 94.

Disposed on the second end of tube 96 is a Y-coupling 100 having three sections (or arms) 100a, 100b, 100c. According the invention, section 100a is adapted to slideably receive the second end of tube 96, section 100c is adapted to slideably receive the first end of tube 104, and section 100b is adapted to engage and, hence, communicate with the sound compensating means 105 (i.e., tube 98) of the invention.

As illustrated in FIG. 8, section 100a of the Y-coupling 100 includes lumen 101 that also extends into and through sections 100b and 100c and, hence, is in communication with lumens 97, 102 when the tubes 96, 104 are operatively engage thereto.

Disposed between tubes 104 and 110 is L-coupling 106. The L-coupling 106 includes a first section 106b adapted to slideably engage the second end of tube 104 and a second section 106a adapted to slideably engage the first end of tube 110.

As illustrated in FIG. 8, the L-coupling 106 also includes a lumen 107 therein that extends into and through L-coupling sections 106a, 106b and, hence, is in communication with lumens 102, 111 when tubes 104, 110 are operatively engaged thereto.

Figure 9:
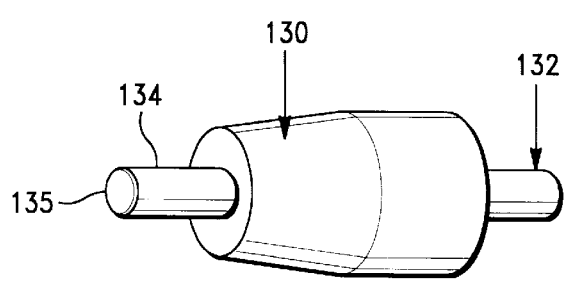
FIG. 9 is a perspective view of the earpiece adapter according to the invention.

Referring back to FIG. 7, disposed on the second end of tube 110 is the earpiece adapter 130. Referring now to FIG. 9, the earpiece adapter 130 includes an inlet 132, outlet 134, and a lumen 135 disposed therein.

Figure 11:
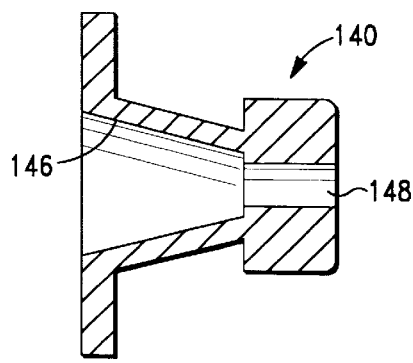
FIG. 11 is a sectional plan view of the earpiece shown in FIG. 10.

As illustrated in FIG. 7, the inlet 132 is adapted to slideably receive the second end of tube 110 and the outlet 134 is adapted to slideably engage the earpiece outlet 148 when the adapter 130 is positioned in the earpiece cavity 146 (see FIG. 11). Earpiece adapter lumen 135 is thus in communication with lumens 111 and earpiece outlet 148 when the tube 110 and earpiece 140 are operatively engaged to the earpiece adapter 130.

As will be appreciated by one having ordinary skill the art, various coupler and coupling arrangements may be employed within the scope of the invention to facilitate communication by and between the input 82, tubes 88, 96, 104, 110 and the earpiece 140. However, as discussed in detail below, the effective attenuation of the first attenuation means 81a is a function of and, hence, directly dependent on the lengths and internal volumes of the tubes 88, 96, 104, 110 and, in particular, the effective (total) volume of lumens 90, 93a, 97, 101, 102, 107, 111, 135 (hereinafter referred to as "the effective volume or signal path of the first attenuation means").

The second attenuation means of the invention 81b comprises a fifth tube 114, having a lumen 115 therein, and a sixth tube 118 that is substantially sealed on a first end 121 and similarly has a lumen 120 therein. As illustrated in FIG. 7, the first end of tube 114 is adapted to slideably engage T-coupling 92.

Disposed between tubes 114 and 118 is coupling 116. According to the invention, coupling 116 is adapted to slideably receive the second ends of tubes 114 and 118.

As illustrated in FIG. 7, coupling 116 includes a lumen 117 therein that is in communication with lumens 115, 120 and, hence, the first attenuation means signal path, when the tubes 114, 118 are operatively connected to coupling 116.

As discussed in detailed below, the effective attenuation of the second attenuation means 81b is a function of and, hence, directly dependent on the lengths and internal volumes of tubes 114, 118 and coupling 116 and, in particular, the effective (total) volume of lumens 115, 117, 120 (hereinafter referred to as "the effective volume or signal path of the second attenuation means").

The sound compensating means of the invention comprises a seventh tube 98 that similarly has a lumen 99 therein. As illustrated in FIG. 7, the first end of the tube 98 is adapted to slideably engage Y-coupling section 100b, whereby lumen 99 is in communication with Y-coupling lumen 101 and, hence, earpiece outlet 148. The second end of tube 98 is preferably open.

The first and second attenuation means 81a, 81b of the invention will now be described in greater detail with reference to FIG. 12. Referring first to curve D, there is shown an illustrative acoustic spectrum of a prior art coupling system.

As illustrated by curve D, the acoustic spectrum of the prior art system typically exhibits a fluctuation in sound intensity, db, (designated D') within the optimum hearing test frequency range (i.e., approx. 100 Hz to 5 KHz). The noted fluctuation in sound intensity can, and in many instances will, have an adverse impact on the hearing test protocol.

An additional drawback of the prior art system is that the system is susceptible to further fluctuations in sound intensity (db) by virtue of the size of the subject's ear. It is well known that although a larger ear only tends to attenuate sound intensity a few db's (i.e., curve D), the effective attenuation of a smaller ear (i.e., curve E) can be, and in many instances is, significant. Indeed, the resulting variation in sound intensity (designated A db) from a large ear (i.e., adult) to a small ear (i.e., infant), can be as much as 9 db, which can similarly pose problems during a hearing test.

Referring now to curves A and B, there are shown illustrative acoustic spectrums for the first attenuation means (curve A)—i.e., an open ended substantially continuous tube having an effective (lumen) volume—and second attenuation means (curve B)—i.e., a closed end substantially continuous tube having an effective (lumen) volume.

As illustrated by curve A, the first attenuation means attenuates higher frequency sound much more quickly than lower frequency sound. In contrast, the second attenuation means attenuates lower frequency sound more than high frequency sound. The net result of the combined system is that the second attenuation means (i.e., closed end tube) compensates for the exaggerated high frequency sound loss in the first attenuation means (i.e., open ended tube) to yield a balanced acoustic spectrum (curve C).

Figure 12:
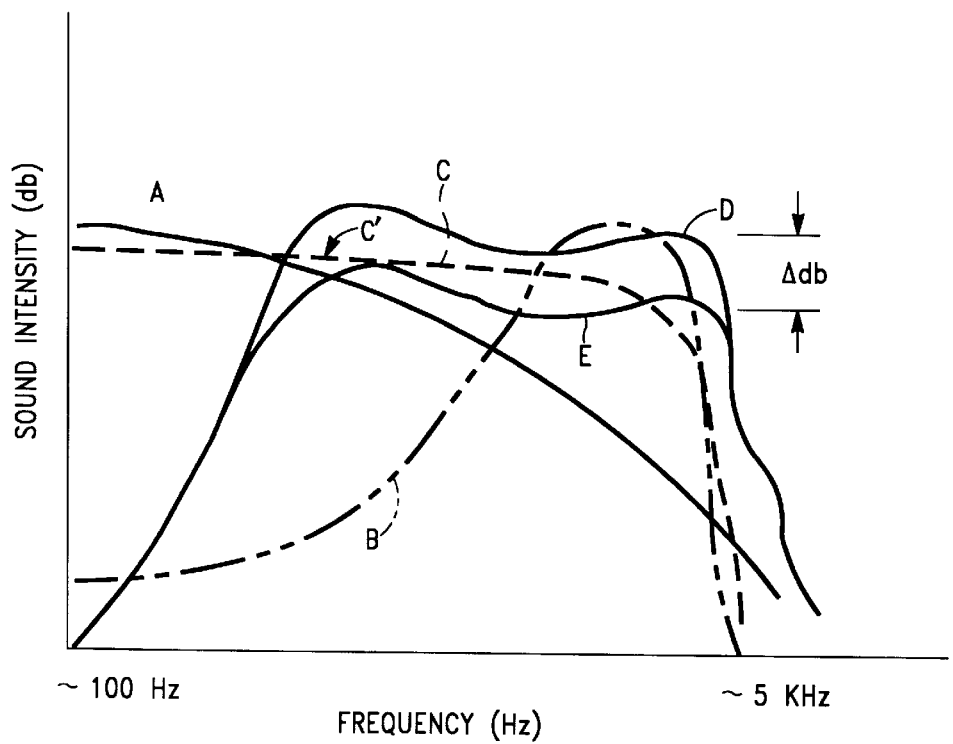
FIG. 12 is a graphical illustration of various signal transfer functions, showing the sound and frequency characteristics of several acoustic stimuli.

As illustrated in FIG. 12, the acoustic spectrum of curve C exhibits a substantially uniform spectrum (or transfer function), designated $C_1$, over the optimum test frequency range of approx. 100 Hz to 5 KHz. The noted spectrum is also substantially stable and is substantially less susceptible to variations in sound intensity from subject to subject than prior art systems. Indeed, Applicant has found that the maximum variation in sound intensity is generally $\leqq 1$ db, which is unparalleled in the art.

A further unique feature of the invention is the sound or signal compensating means (i.e., signal compensator) 105. It is well known in the art that the compensating volume using an "over the ear coupler" is primarily a function of the volume of the ear (i.e., Pinna). Thus, the sound intensity that is transmitted to the inner ear is a function of and, hence, directly dependent on the volume of the ear pinna 5 (see FIG. 13).

To compensate for small ear pinna volume (i.e., infant), open ended tube 98 is provided. As indicated above, tube 98 includes lumen 99 having a fixed length, which provides a compensating or reference volume for the system.

In a preferred embodiment of the invention, the sound compensating means provides selective reduction or enhancement of the response signal volume in the range of 50 to 90%.

It will be appreciated that the present invention may be employed with virtually all conventional hearing screening devices, such as the ALGO 1E™ and ALGO 2 hearing screening systems available from Natus Medical, as well as acoustic emission based systems.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An acoustic coupling apparatus for a hearing screening device adapted to transmit a first acoustic stimulus, said first acoustic stimulus having at least first and second frequencies, said acoustic coupling apparatus comprising:
    a coupling input adapted to engage said hearing screening device, said coupling input being adapted to receive said first acoustic stimulus and transmit at least a second response signal to said hearing screening device;
    at least a first earpiece adapted to be disposed proximate the ear canal of one of the ears of a subject, said earpiece including a stimulus input adapted to transmit at least a second acoustic stimulus to said subject and receive at least a first response signal from said ear of the subject, said first response signal having a first volume;
    a first passive attenuator adapted to attenuate said first frequency of said first acoustic stimulus;
    a second passive attenuator adapted to attenuate said second frequency of said first acoustic stimulus,
    said first and second passive attenuators in combination providing said second acoustic stimulus having a substantially balanced acoustic spectrum; and
    a response signal compensator adapted to regulate said first volume of said first response signal and provide said second response signal.

2. The apparatus of claim 1, wherein said first frequency is in the range of 2 KHz to 10 KHz.

3. The apparatus of claim 2, wherein said first attenuator attenuates said first frequency in the range of approximately 50 to 90%.

4. The apparatus of claim 1, wherein said second frequency is in the range of 500 Hz to 3 KHz.

5. The apparatus of claim 4, wherein said second attenuator attenuates said second frequency in the range of approximately 50 to 90%.

6. The apparatus of claim 1, wherein said second acoustic stimulus has a substantially balanced acoustic spectrum.

7. An acoustic coupling apparatus for a hearing screening device adapted to transmit a first acoustic stimulus and receive at least one response signal from a subject, said first acoustic stimulus having at least first and second frequencies, said acoustic coupling apparatus comprising:
    a coupling input adapted to removeably engage said hearing screening device, said coupling input being adapted to receive said first acoustic stimulus and transmit at least a second response signal from said subject to said hearing screening device;
    first attenuation means for attenuating said first frequency of said first acoustic stimulus, said first attenuation means having a first signal path in communication with said coupling input, said first signal path adapted to receive said first acoustic stimulus;
    second attenuation means for attenuating said second frequency of said first acoustic stimulus, said second attenuation means having a second signal path in communication with said first signal path,
    said first and second attenuation means in combination providing a second acoustic stimulus having a substantially balanced acoustic spectrum;
    at least a first earpiece adapted to be disposed proximate the ear canal of one of the ears of said subject, said earpiece including a stimulus input in communication with at least said first signal path, said stimulus input being adapted to transmit at least said second acoustic stimulus to said subject and receive at least a first response signal from said subject, said first response signal having at least a first volume; and
    a response signal regulator, said response signal regulator being adapted to regulate said first volume and provide said second response signal.

8. The apparatus of claim 7, wherein said first frequency is in the range of 2 KHz to 10 KHz.

9. The apparatus of claim 8, wherein said first attenuation means attenuates said first frequency in the range of approximately 50 to 90%.

10. The apparatus of claim 7, wherein said second frequency is in the range of 500 Hz to 3 KHz.

11. The apparatus of claim 10, wherein said second attenuation means attenuates said second frequency in the range of approximately 50 to 90%.

12. The apparatus of claim 7, wherein said response signal regulator is adapted to reduce said first volume in the range of approximately 50 to 90%.

13. The apparatus of claim 7, wherein said response signal regulator is adapted to increase said first volume in the range of approximately 50 to 90%.

14. A method of testing the hearing of a subject, comprising the steps of:
    presenting a first acoustic stimulus to a first passive attenuator, said first acoustic stimulus having at least first and second frequencies;
    passively attenuating said first and second frequencies with first and second passive attenuators to yield at least a second acoustic stimulus having a substantially balanced acoustic spectrum;
    transmitting said second acoustic stimulus to the inner ear of said subject;

detecting a first response signal from said subject's inner ear, said first response signal having a first volume;

regulating said first volume to a pre-selected second volume; and detecting said first response signal having said second volume.

* * * * *